US012766262B2

(12) United States Patent
Carlsson et al.

(10) Patent No.: US 12,766,262 B2
(45) Date of Patent: Oct. 20, 2026

(54) MEDICAMENT DELIVERY DEVICE

(71) Applicant: SHL Medical AG, Zug (CH)

(72) Inventors: Daniel Carlsson, Nacka Strand (SE); Yen-Tung Chen, Taoyuan City (TW)

(73) Assignee: SHL Medical AG, Zug (CH)

(*) Notice: Subject to any disclaimer, the term of this patent is extended or adjusted under 35 U.S.C. 154(b) by 385 days.

(21) Appl. No.: 18/700,783

(22) PCT Filed: Oct. 6, 2022

(86) PCT No.: PCT/EP2022/077871
§ 371 (c)(1),
(2) Date: Apr. 12, 2024

(87) PCT Pub. No.: WO2023/066678
PCT Pub. Date: Apr. 27, 2023

(65) Prior Publication Data

US 2024/0399062 A1 Dec. 5, 2024

(30) Foreign Application Priority Data

Oct. 19, 2021 (EP) .................................... 21203581

(51) Int. Cl.
*A61M 5/20* (2006.01)
*A61M 5/315* (2006.01)
*A61M 5/32* (2006.01)

(52) U.S. Cl.
CPC ........ *A61M 5/2033* (2013.01); *A61M 5/3158* (2013.01); *A61M 5/3234* (2013.01)

(58) Field of Classification Search
CPC .............. A61M 5/2033; A61M 5/3158; A61M 5/3234; A61M 5/3204; A61M 5/46;
(Continued)

(56) References Cited

U.S. PATENT DOCUMENTS

2013/0138048 A1* 5/2013 Kemp ................. A61M 5/2033 604/196
2014/0323978 A1* 10/2014 Henley ................... A61M 5/20 604/218
2019/0336689 A1* 11/2019 Montgomery ...... A61M 5/3234

OTHER PUBLICATIONS

International Search Report and Written Opinion for corresponding PCT application No. PCT/EP2022/077871 dated Dec. 5, 2022.

* cited by examiner

*Primary Examiner* — Dung T Ulsh
(74) *Attorney, Agent, or Firm* — McDonnell Boehnen Hulbert & Berghoff LLP

(57) ABSTRACT

The present disclosure provides a medicament delivery device configured to expel a medicament from a medicament container comprising an injection needle. The medicament delivery device is configured to assume a retracted state in which an injection needle is arranged inside a medicament delivery member and prevented from external exposure, and a protracted state in which the injection needle is configured to protrude proximally from the proximal end of the medicament delivery member. When the medicament delivery device transition from the retracted state to the protracted state, the medicament delivery member is arranged stationary relative to a housing. The syringe collar is axially locked to a surface portion of the housing when the medicament delivery device assumes the protracted state such that an axial force from the syringe collar, generated during the transition from the retracted state to the protracted state, is absorbed by the surface portion of the housing.

13 Claims, 9 Drawing Sheets

(58) Field of Classification Search
CPC .. A61M 5/3243; A61M 5/326; A61M 5/3272; A61M 2005/206; A61M 2005/208
See application file for complete search history.

F
402
120
404
304
116
118
306

F
120
304
116
118
302
404
406
100

MEDICAMENT DELIVERY DEVICE

CROSS-REFERENCE TO RELATED APPLICATIONS

The present application is a U.S. National Phase Application pursuant to 35 U.S.C. § 371 of International Application No. PCT/EP2022/077871 filed Oct. 6, 2022, which claims priority to European Patent Application No. 21203581.0 filed Oct. 19, 2021. The entire disclosure contents of these applications are herewith incorporated by reference into the present application.

TECHNICAL FIELD

The present disclosure generally relates to a medicament delivery device configured to expel medicament from a medicament container.

BACKGROUND

A number of medical conditions require reliable provision of a medicament from a medicament delivery device. The medicament is typically comprised in a medicament container within the medicament delivery device, the medicament container being configured to expel the medicament via some type of delivery member, such as a needle or a nozzle.

These days, a number of different medicament delivery devices exist, including various types of injectors (for example pen injectors, autoinjectors, on-body devices). Although many of these devices have enabled major improvements in the management of a number of medical conditions, various drawbacks do still exist in the current technology.

According to an example, the medicament delivery device often comprises a needle cover protruding out from a housing and is arranged to cover an injections needle before usage. When pressing the medicament delivery device, and in particular the needle cover, onto e.g. the skin of a medicament recipient, the needle cover is pushed into housing of the medicament delivery device. The needle cover is still arranged in abutment with the skin of the medicament recipient. Thereafter, the needle is protracted out from the needle cover and inserted through the skin of the medicament recipient by actuation of the medicament delivery device, whereafter the medicament is subsequently delivered through the injection needle into the medicament recipient. However, due to the mechanical interaction between the components of the medicament delivery device, the needle cover sometimes moves slightly out from the housing when actuating the medicament delivery device. The needle cover may hereby generate an unpleasant kick back force on the skin of the medicament recipient. The kick back force may be generated by the motion of a so-called syringe collar interacting with the needle cover. The kick back force may also be generated by a proximal end portion of a plunger rod forcing medicament out of the medicament container.

Medicament delivery devices are thus in need of further improvement, in particular when it comes to comfort for the users of medicament delivery devices.

SUMMARY

The invention is defined by the appended claims, to which reference should now be made. An object of the present disclosure is thus to provide a medicament delivery device which solves, or at least mitigates, problems of the prior art.

In the present disclosure, when the term "distal direction" is used, this refers to the direction pointing away from the dose delivery site during use of the medicament delivery device. When the term "distal part/end" is used, this refers to the part/end of the delivery device, or the parts/ends of the members thereof, which under use of the medicament delivery device is/are located furthest away from the dose delivery site. Correspondingly, when the term "proximal direction" is used, this refers to the direction pointing towards the dose delivery site during use of the medicament delivery device. When the term "proximal part/end" is used, this refers to the part/end of the delivery device, or the parts/ends of the members thereof, which under use of the medicament delivery device is/are located closest to the dose delivery site.

Further, the term "longitudinal", "longitudinally", "axially" or "axial" refer to a direction extending from the proximal end to the distal end, typically along the device or components thereof in the direction of the longest extension of the device and/or component.

Similarly, the terms "transverse", "transversal" and "transversally" refer to a direction generally perpendicular to the longitudinal direction.

Further, the terms "circumference", "circumferential", or "circumferentially" refer to a circumference or a circumferential direction relative to an axis, typically a central axis extending in the direction of the longest extension of the device and/or component. Similarly, "radial" or "radially" refer to a direction extending radially relative to the axis, and "rotation", "rotational" and "rotationally" refer to rotation relative to the axis.

According to a first aspect of the present disclosure there is provided a medicament delivery device configured to expel a medicament from a medicament container comprising an injection needle, the medicament delivery device comprising a housing, a medicament delivery member having a tubular body extending along an axis in an axial direction from a proximal end to a distal end, the medicament delivery member comprises an opening configured to receive the medicament container, wherein the medicament delivery member is axially movable within the housing, a syringe collar at least partly enclosed by the medicament delivery member, wherein the medicament delivery member and the syringe collar are axially movable within the housing relative to each other, and a medicament delivery member spring arranged between, and in contact with, the medicament delivery member and the syringe collar, wherein the medicament delivery device is configured to assume a retracted state in which the injection needle is arranged inside the medicament delivery member and prevented from external exposure, and a protracted state in which the injection needle is configured to protrude proximally from the proximal end of the medicament delivery member, wherein, when the medicament delivery device transition from the retracted state to the protracted state, the medicament delivery member is arranged stationary relative to the housing and the syringe collar is arranged to move relative to the medicament delivery member in a proximal direction and compress the medicament delivery member spring against the medicament delivery member, and wherein the syringe collar is axially locked to a surface portion of the housing when the medicament delivery device assumes the protracted state such that an axial force from the syringe collar, generated during the transition from the retracted state to the protracted state, is absorbed by the surface portion of the housing.

The wording medicament delivery member should be construed as a member arranged to prevent exposure of a needle. Thus, before and after usage of the medicament delivery device, the medicament delivery member prevents a user of the medicament delivery device to accidentally be stung by the needle. The medicament delivery member may also be referred to as a needle cover.

Further, the definition “syringe collar is axially locked to a surface portion of the housing” should be construed as the syringe collar is directly locked to the surface portion of the housing as well as that the syringe collar is indirectly locked to the surface portion of the housing via another member of the medicament delivery device. The syringe collar may thus be arranged in mechanical contact with the surface portion of the housing when the syringe collar is axially locked to the surface portion. The syringe collar may alternatively be connected to the surface portion of the housing via e.g. a rotator of the medicament delivery device.

The present invention is based on the insight that by arranging the medicament delivery member stationary relative to the housing as well as to axially lock the syringe collar axially to the surface portion of the housing, the kick back force is not directed into the skin medicament recipient, but instead absorbed by the housing. Hereby, the user of the medicament delivery device will feel a slight kick back force in his/her hand, which is less unpleasant compared to absorbing the kick back force by the skin in the vicinity of the inserted needle.

According to an example embodiment, the medicament delivery device may further comprise a rotator having a distal end and a proximal end, wherein the rotator is arranged within a portion of the housing.

According to an example embodiment, the medicament delivery member may comprise a protrusion at the distal end of the medicament delivery member, the protrusion being arranged in a first axially extending track of the rotator, wherein the protrusion and a distal end portion of the first axially extending track of the rotator are arranged at a distance from each other when the medicament delivery device assumes the protracted state.

When the medicament delivery member is pressed against e.g. the skin of the medicament recipient, the medicament delivery member is moved distally relative to the rotator, and the protrusion of the medicament delivery member is pressed against an inclined surface of the first axially extending track. Due to the interaction between the protrusion and the inclined surface of the first axially extending track, the rotator will rotate simultaneously as the protrusion moves distally. By arranging the protrusion and the distal end portion of the first axially extending track at a distance from each other when the medicament assumes the protracted state, no force will be transmitted between the rotator and the medicament delivery member, thus preventing the kick back force to be absorbed by the skin of the medicament recipient.

According to an example embodiment, the syringe collar may comprise a radially extending protrusion.

According to an example embodiment, the radially extending protrusion of the syringe collar may be arranged in abutment with a proximal end portion of an axially extending track of the portion of the housing when the medicament delivery device assumes the protracted state. When the medicament delivery device transitions from the retracted state to the protracted state, the movement of the syringe collar will be stopped by the interaction between the radially extending protrusion of the syringe collar and the proximal end portion of the axially extending track of the portion of the housing, whereby the kick back force will be absorbed by the housing portion at the proximal end portion of the axially extending track of the portion of the housing.

Accordingly, and according to an example embodiment, the radially extending protrusion of the syringe collar is arranged in the axially extending track of the portion of the housing and axially movable along the axially extending track during the transition from the retracted state to the protracted state.

According to an example embodiment, the housing may comprise a first housing portion and a second housing portion arranged in contact with each other, the first housing portion being arranged to at least partly house the medicament delivery member, and the second housing portion is arranged distally from the first housing portion and configured to be held by the hand of a user. Furthermore, and according to an example embodiment, the surface portion of the housing may be arranged on the first housing portion. Since the first and second housing portions are arranged in contact with each other, i.e. they are in axial abutment with each other, the kick back force will be transmitted into the first housing portion and absorbed by the user's hand holding the second housing portion.

According to an example embodiment, the rotator may comprise a second axially extending track, the second axially extending track comprising an inclined surface portion, wherein the radially extending protrusion of the syringe collar is arranged in the second axially extending track and arranged to follow the inclined surface portion when the medicament delivery device transitions from the retracted state to the protracted state.

According to an example embodiment, the radially extending protrusion of the syringe collar may be arranged in abutment with the inclined surface portion of the rotator when the syringe collar follows the inclined surface portion, thereby forcing the rotator to be moved in a proximal direction and to rotate around an axially extending geometric center axis of the medicament delivery device.

According to an example embodiment, the radially extending protrusion of the syringe collar may be arranged in abutment with a proximal end portion of the second axially extending track when the medicament delivery device assumes the protracted state. When the medicament delivery device transitions from the retracted state to the protracted state, and the radially extending protrusion of the syringe collar finally is arranged in abutment with the proximal end portion of the second axially extending track, the force from the motion of the syringe collar is absorbed by the rotator. As described above, the protrusion of the medicament delivery member may be arranged at a distance from the distal end portion of the first axially extending track of the rotator. The force generated from the motion of the syringe collar will thus not be absorbed by the medicament delivery member. Further, and as also described above, when the radially extending protrusion of the syringe collar is arranged in abutment with the proximal end portion of the axially extending track of the portion of the housing, the force from generated from the motion of the syringe collar will also not be absorbed by the medicament delivery member.

According to an example embodiment, the proximal end of the rotator may comprise a surface portion arranged in abutment with a distally facing surface portion of the housing when the medicament delivery device assumes the protracted state. Hereby, any axial forces generated in the rotator during the transition from the protracted state to the retracted state can be absorbed by the housing at the distal facing surface portion.

According to an example embodiment, the medicament delivery device may further comprise a plunger rod configured to interact with the syringe collar. When the plunger rod interacts with the syringe collar, the plunger rod preferably interacts with the syringe collar via the medicament container. Thus, the plunger rod interacts with the medicament container, i.e. the plunger rod is arranged in mechanical contact with the medicament container. The medicament container is in turn interacting with the syringe collar, i.e. the medicament container and the syringe collar are in mechanical contact with each other.

According to an example embodiment, the medicament delivery device may further comprise a plunger spring connected to a proximal end portion of the plunger rod, the plunger spring being pre-tensioned when the medicament delivery device assumes the retracted state, and arranged to exert a force on the proximal end portion of the plunger rod to force the plunger rod towards the medicament container during the transition from the retracted state to the protracted state.

The plunger rod is preferably moved in the proximal direction when the medicament delivery device transitions from the retracted state to the protracted state for forcing medicament out from the medicament container.

According to an example embodiment, the medicament delivery device may further comprise an activation mechanism, the medicament delivery device being arranged to transition from the retracted state to the protracted state upon actuation of the activation mechanism. The activation mechanism is preferably arranged at a distal end portion of the medicament delivery device and accessible by e.g. the thumb of the hand holding the medicament delivery device.

Generally, all terms used in the claims are to be interpreted according to their ordinary meaning in the technical field, unless explicitly defined otherwise herein. All references to "a/an/the member, apparatus, component, means, etc." are to be interpreted openly as referring to at least one instance of the member, apparatus, component, means, etc., unless explicitly stated otherwise.

BRIEF DESCRIPTION OF THE DRAWINGS

The specific embodiments of the inventive concept will now be described, by way of example, with reference to the accompanying drawings, in which.

DETAILED DESCRIPTION

The inventive concept will now be described more fully hereinafter with reference to the accompanying drawings, in which exemplifying embodiments are shown. The inventive concept may, however, be embodied in many different forms and should not be construed as limited to the embodiments set forth herein; rather, these embodiments are provided by way of example so that this disclosure will be thorough and complete, and will fully convey the scope of the inventive concept to those skilled in the art. Like numbers refer to like members throughout the description.

Figure 1A:
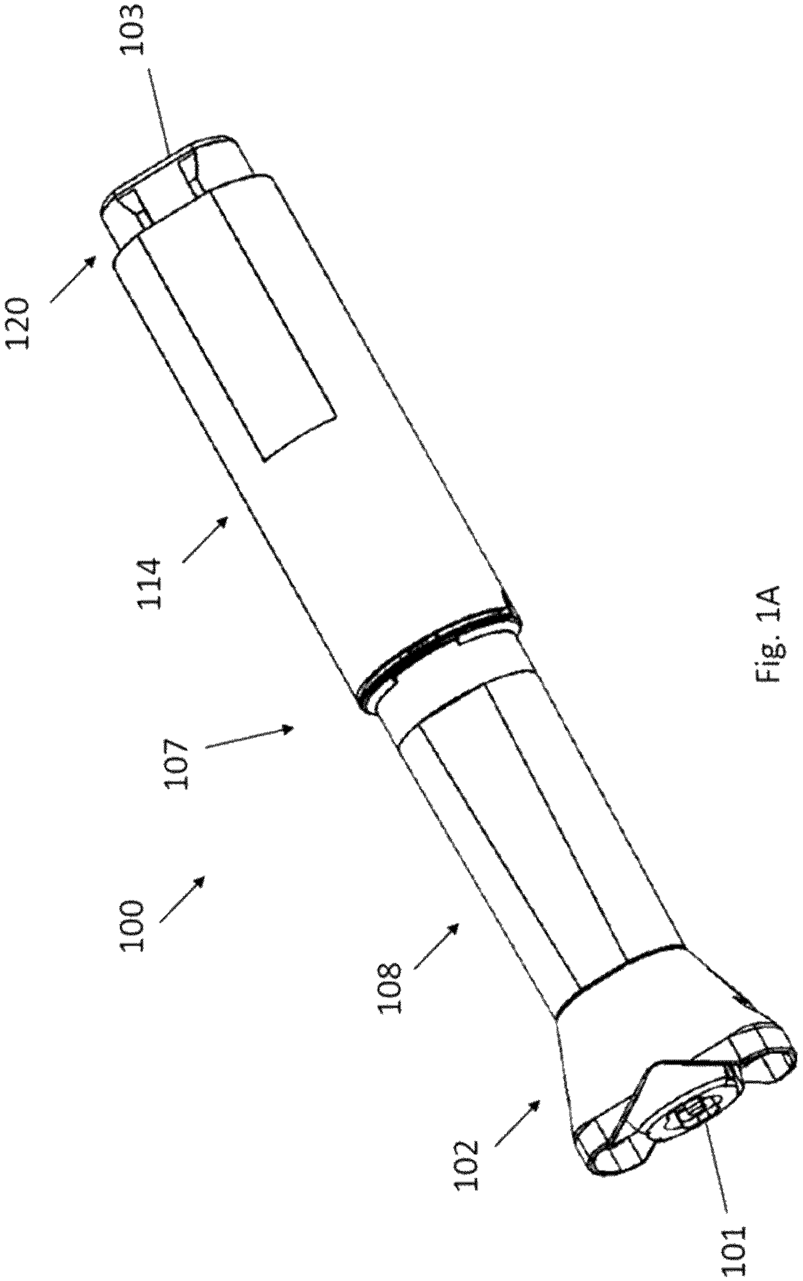
FIG. 1A is a schematic illustration of a medicament delivery device according to an example embodiment.
Figure 1B:
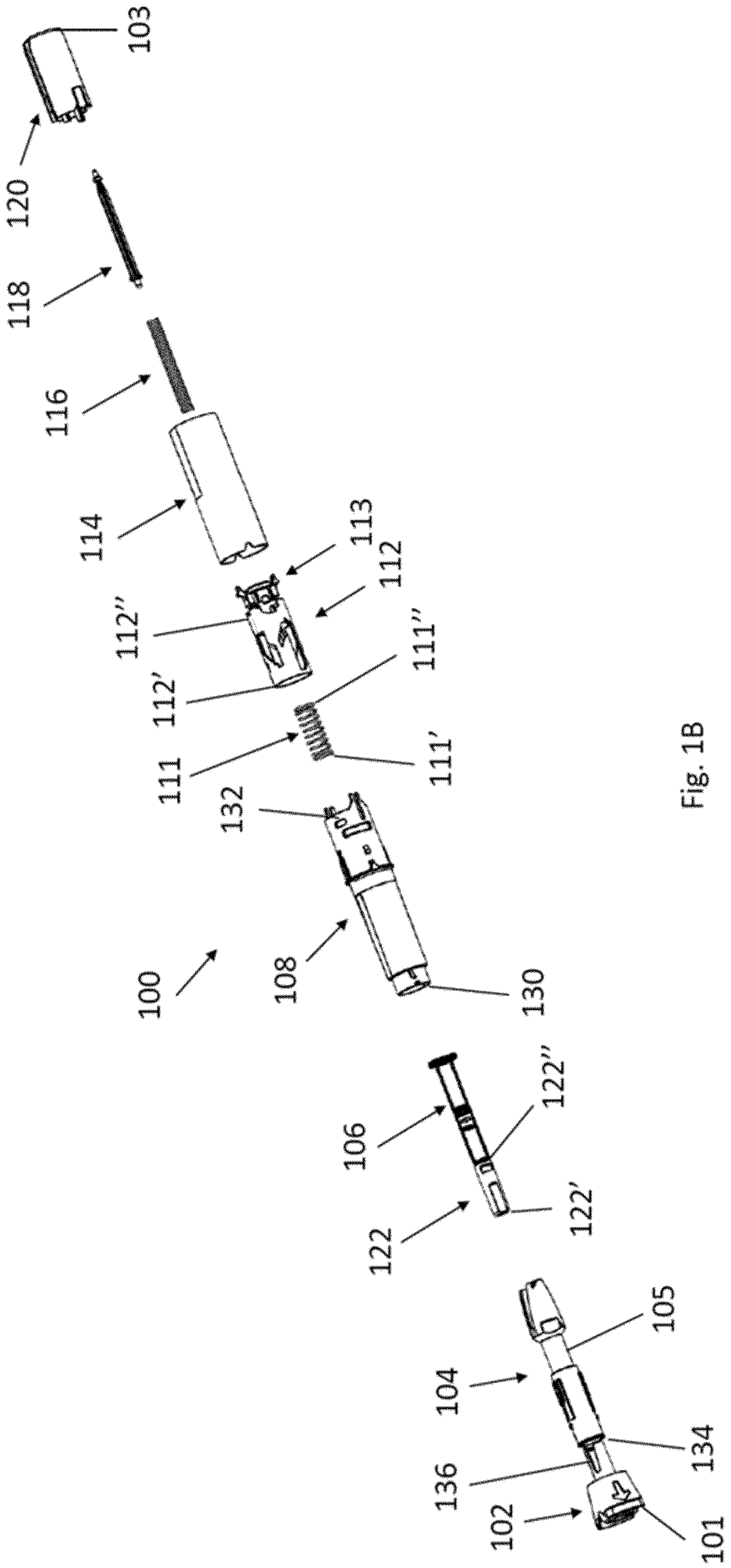
FIG. 1B is an exploded view of the medicament delivery device in FIG. 1 according to an example embodiment.

Reference is made to FIGS. 1A-1B, in which FIG. 1A is a schematic illustration of a medicament delivery device 100, and FIG. 1B is an exploded view of the medicament delivery device 100 according to an example embodiment. As can be seen, the medicament delivery device 100 extends in an axial direction between a proximal end 101 and a distal end 103. The medicament delivery device 100 comprises a needle cap 102, a medicament delivery member 104, in the following and throughout the remaining description referred to as a needle cover 105, a medicament container 106, and a housing 107 comprising a first housing portion 108 and a second housing portion 114. The medicament delivery device 100 further comprises a medicament delivery member spring 110, in the following referred to as a needle cover spring 111, a rotator 112 having a proximal end 112' and a distal end 112", a syringe collar 113, a plunger spring 116, a plunger rod 118 and an activation mechanism 120. As illustrated in FIG. 1B, the needle cover spring 111 has a proximal end 111' and a distal end 111".

The needle cap 102 is arranged at the proximal end 101 of the medicament delivery device 100 and is provided as a cover before usage of the medicament delivery device 100. In further detail, the needle cap 102 prevents components, such as a rigid needle shield 122 and an injection needle (202 in e.g. FIG. 2A), from being exposed before the medicament delivery device 100 is prepared for usage. Before usage of the medicament delivery device 100, the injection needle is housed within the rigid needle shield 122 and the needle cap 102 is attached to a proximal end 130 of the first housing portion 108, wherein a proximal portion 122' of the rigid needle shield 122 and a proximal end 134 of the needle cover 105 is housed within the needle cap 102.

The needle cap 102 also comprises an axially elongated portion 136. The axially elongated portion 136 extends distally and is arranged radially between the needle cover 105 and the rigid needle shield 122. In particular, the axially elongated portion 136 is at a distal end (not shown) attached to a distal end 122" of the rigid needle shield 122. When the needle cap 102 is removed, i.e. moved proximally in the axial direction, the attachment between the axially elongated portion 136 of the needle cap 102 and the distal end 122" of the rigid needle shield 122 causes also the rigid needle shield 122 to be moved proximal in the axial direction and subsequently removed.

Figure 2B:
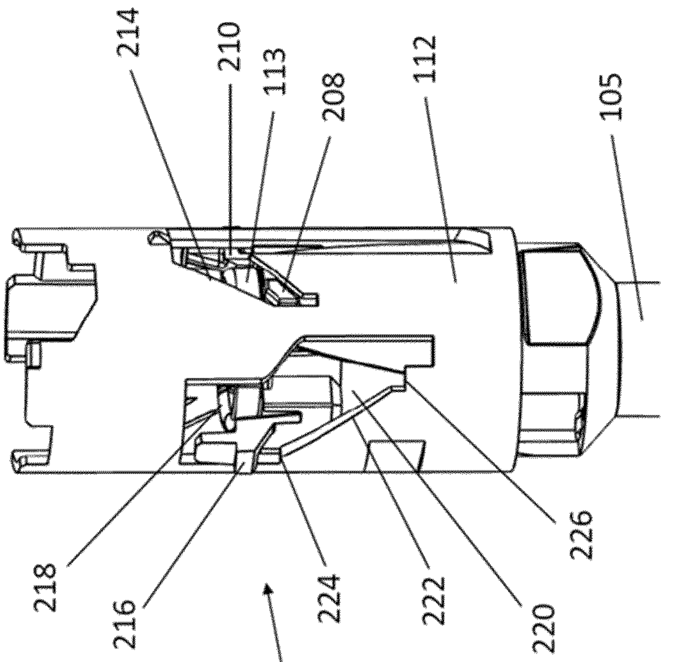
FIG. 2A-2B illustrate an example embodiment of the medicament delivery device in a cross-sectional view of and a detailed perspective view in a state when a cap is removed.
Figure 2A:
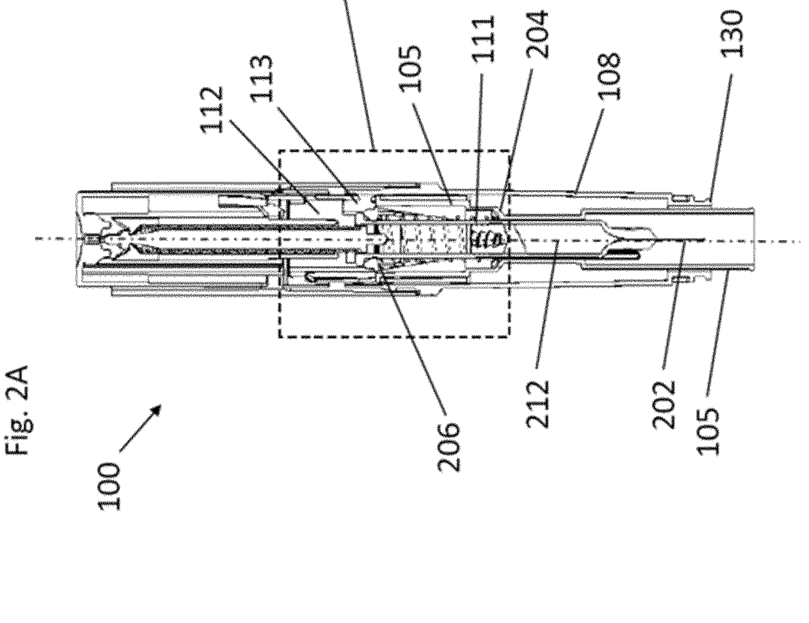

The interaction between the above described components will be evident from the below disclosure detailing the functionality of the medicament deliver device 100 with reference to FIGS. 2A-6. Reference is initially made to FIGS. 2A-2B in which FIG. 2A is a cross-sectional view of the medicament delivery device 100 when the above described needle cap 102 is removed, while FIG. 2B is a detailed perspective view illustrating only the above described rotator 112, the needle cover 105 and the syringe collar 113 according to an example embodiment. As described above, when the needle cap 102 is removed, also the rigid needle shield 122 is removed. As such, the needle cap 102 and the rigid needle shield 122 are both removed when the medicament delivery device 100 is arranged in the state depicted in FIGS. 2A-2B.

As can be seen in FIG. 2A, the syringe needle 202 is arranged inside the needle cover 105. The needle cover 105 is movable and the tip of the syringe needle 202 is protected by the first housing portion 108 and there is at this stage no risk of being accidentally stung by the syringe needle 202. Further, the needle cover 105 protrudes proximally from the proximal end 130 or the first housing portion 108.

The needle cover spring 111 is supported between a radially extending floor portion 204 of the needle cover 105 and a spring abutment surface 206 of the syringe collar 113. In detail, the proximal end 111' of the needle cover spring 111 is arranged in abutment with the radially extending floor portion 204 of the needle cover 105 and the distal end 111" of the needle cover spring 111 is arranged in abutment with the spring abutment surface 206 of the syringe collar 113.

With reference to FIG. 2B, the needle cover 105 comprises a protrusion 208. The protrusion 208 is arranged at a distal end 134 of the needle cover 105 and protrudes radially in a distance away from an axially extending geometric center axis 212 of the medicament delivery device 100. The protrusion 208 is arranged in a first axially extending track 210 of the rotator 112. The first axially extending track 210 comprises an inclined surface 214, which inclined surface 214 is, in the state depicted in FIG. 2B, arranged distally from the protrusion 208. The interaction between the protrusion 208 of the needle cover 105 and the inclined surface 214 will be described in further detail below with reference to FIG. 3B.

Furthermore, the syringe collar 113, which is at least partly housed by the rotator 111, i.e. the syringe collar 113 is positioned radially inside the rotator 111, comprises a radially extending protrusion 216. The radially extending protrusion 216 is arranged at a distal end 218 of the syringe collar 113 and extends radially from the distal end 218 in a direction away from the axially extending geometric center axis 212. s extending protrusion 216 is arranged in a second axially extending track 220 of the rotator 112. The second axially extending track 220 comprises an inclined surface portion 222, which inclined surface portion 222 is, in the state depicted in FIG. 2B, arranged proximally from the radially extending protrusion 216 of the syringe collar 113. The second axially extending track 220 comprises an upper ledge portion 224 and a lower ledge portion 226. The upper ledge portion 224 is arranged at a distal end of the inclined surface portion 222 and the lower ledge portion 226 is arranged at a proximal end of the inclined surface portion 222. The inclined surface portion 222 is thus inclined in the axial and circumferential direction of the rotator 112 and extends between the upper 224 and the lower 226 ledge portions.

In the state depicted in FIG. 2B, the radially extending protrusion 216 of the syringe collar 113 is arranged distally from the upper ledge portion 224. Hereby, the syringe collar 113 is prevented from moving in the proximal direction since the radially extending protrusion of syringe collar 216 will interact with the upper ledge portion 224 if the syringe collar 113 would move in such direction.

Figure 3B:
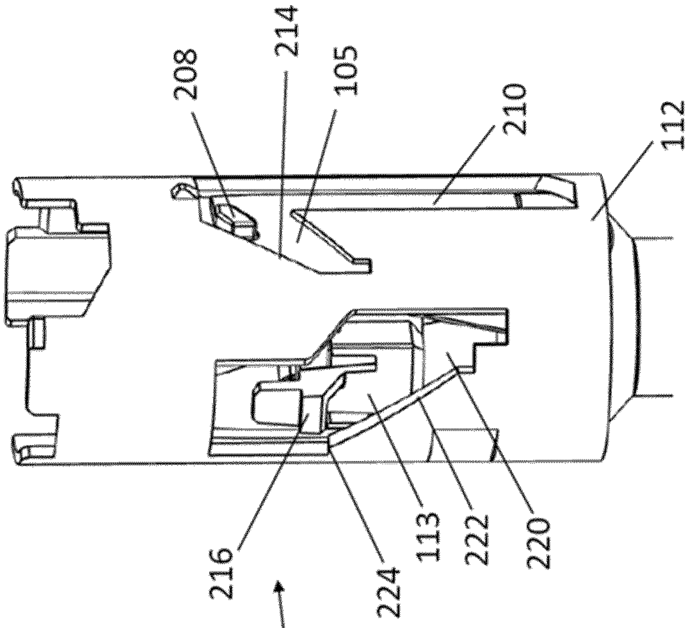
FIGS. 3A-3B illustrate an example embodiment of the medicament delivery device in a cross-sectional view of and a detailed perspective view in a state when the medicament delivery member is pushed against an injection site.
Figure 3A:
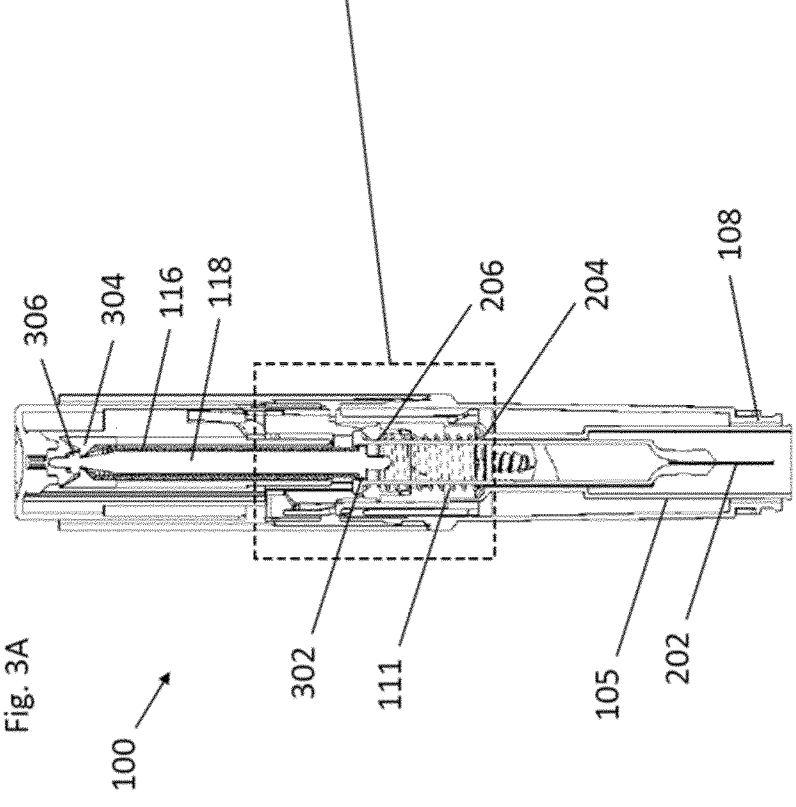

Reference is now made to FIGS. 3A and 3B for describing an example embodiment of the interaction between components of the medicament delivery device 100 when the needle cover is pushed against the dose delivery site. In particular, FIG. 3A is a cross-sectional view of the medicament delivery device 100 when the needle cover 105 is pushed against the dose delivery site, while FIG. 3B is a detailed perspective view illustrating only the interaction between the rotator 112, the needle cover 105 and the syringe collar 113.

As can be seen in FIG. 3A, the needle cover 105 has been moved in the distal direction relative to the first housing portion 108 compared to the embodiment depicted in FIG. 2A. The syringe needle 202 is still arranged within the needle cover 105 and protected from external exposure. When the needle cover 105 is pushed against the dose delivery site as depicted in FIG. 3A, the needle cover spring 111 is further biased between the radially extending floor portion 204 of the needle cover 105 and the spring abutment surface 206 of the syringe collar 113.

As can be seen in FIG. 3B, when the needle cover 105 is moved in the distal direction relative to the first housing portion 108, the protrusion 208 of needle cover 105 interacts with the inclined surface 214 of the first axially extending track 210. Due to the interaction between the protrusion of needle cover 208 and the inclined surface 214 of the first axially extending track 210, the rotator rotates around the axially extending geometric center axis 212 as well as moves slightly in the distal direction. Hereby, the rotator 112 also rotates relative to the radially extending protrusion 216 of syringe collar 113. In detail, the rotator 112, and in particular the upper ledge portion 224 of the rotator 112 rotates circumferentially away from the radially extending protrusion 216 of syringe collar 113. Hereby, the radially extending protrusion 216 of syringe collar 113 is now arranged distally from the inclined surface portion 222 of the second axially extending track 220 and free to move in the proximal direction.

As is also illustrated in FIG. 3A, the plunger spring 116 is pre-compressed between a proximal support portion 302 of the plunger rod 118 and a pair of flexible plunger supporting arms 304. The pair of flexible plunger supporting arms 304 are also supporting a distal support portion 306 of the plunger rod 118. In detail, the plunger spring 116 is arranged on an opposite axial end of the pair of flexible plunger supporting arms 304 compared to the distal support portion 306 of the plunger rod 118.

Figures 4A, 4B:
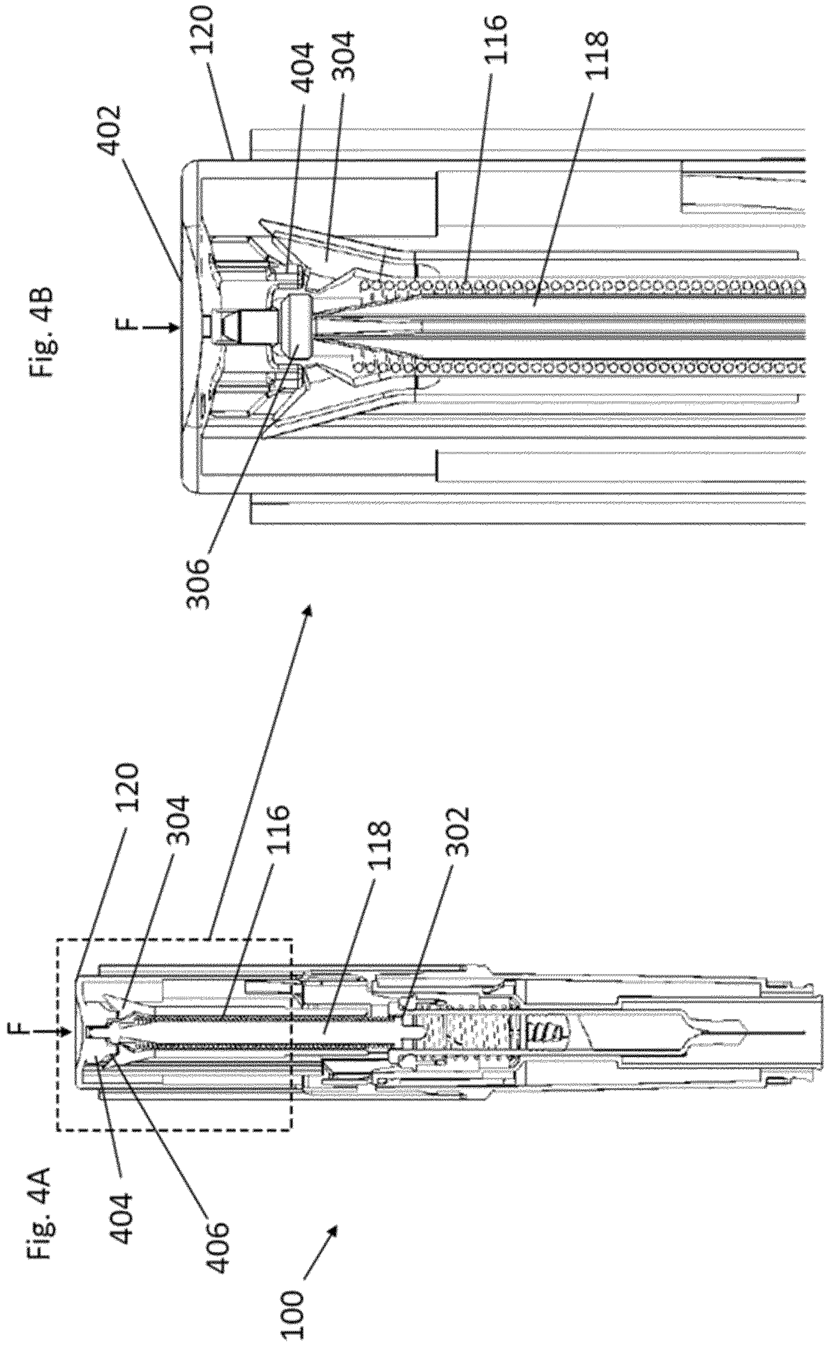
FIGS. 4A-4B illustrate an example embodiment of the medicament delivery device in a cross-sectional view of and a detailed perspective view in a state when an activation mechanism is actuated.

The following will now describe the state when the medicament delivery device 100 is activated to initiate the transition from a retracted state, in which the injection needle 202 is arranged inside the needle cover 105 and prevented from external exposure, to a protracted state in which the injection needle 202 protrudes proximally from the proximal end of the needle cover 105. Reference is therefore made to FIGS. 4A and 4B, where FIG. 4A is a cross-sectional view of the medicament delivery device 100 and FIG. 4B is a detailed illustration of the interaction between the plunger spring 116, the plunger rod 118 and the activation mechanism 120 according to an example embodiment.

As can be seen in FIG. 4A, when the activation mechanism 120 is actuated by a force F acting in the proximal direction on a distal surface 402 of the activation mechanism 120, an activation portion 404 of the activation mechanism 120 is pushed proximally against an outwardly inclined surface 406 of the flexible plunger supporting arms 304. By means of this interaction between the activation portion 404 and the outwardly inclined surface 406, the flexible plunger supporting arms 304 are forced away from the distal support portion 306 of the plunger rod 118. Since the plunger spring 116 is pre-compressed between the proximal support portion 302 of the plunger rod 118 and the pair of flexible plunger supporting arms 304 before actuation of the actuation mechanism 120, the plunger spring 116 is now released to initiate a proximal motion of the plunger rod 118 which will be described in further detail below with reference to FIGS. 5A and 5B.

Figures 5A, 5B:
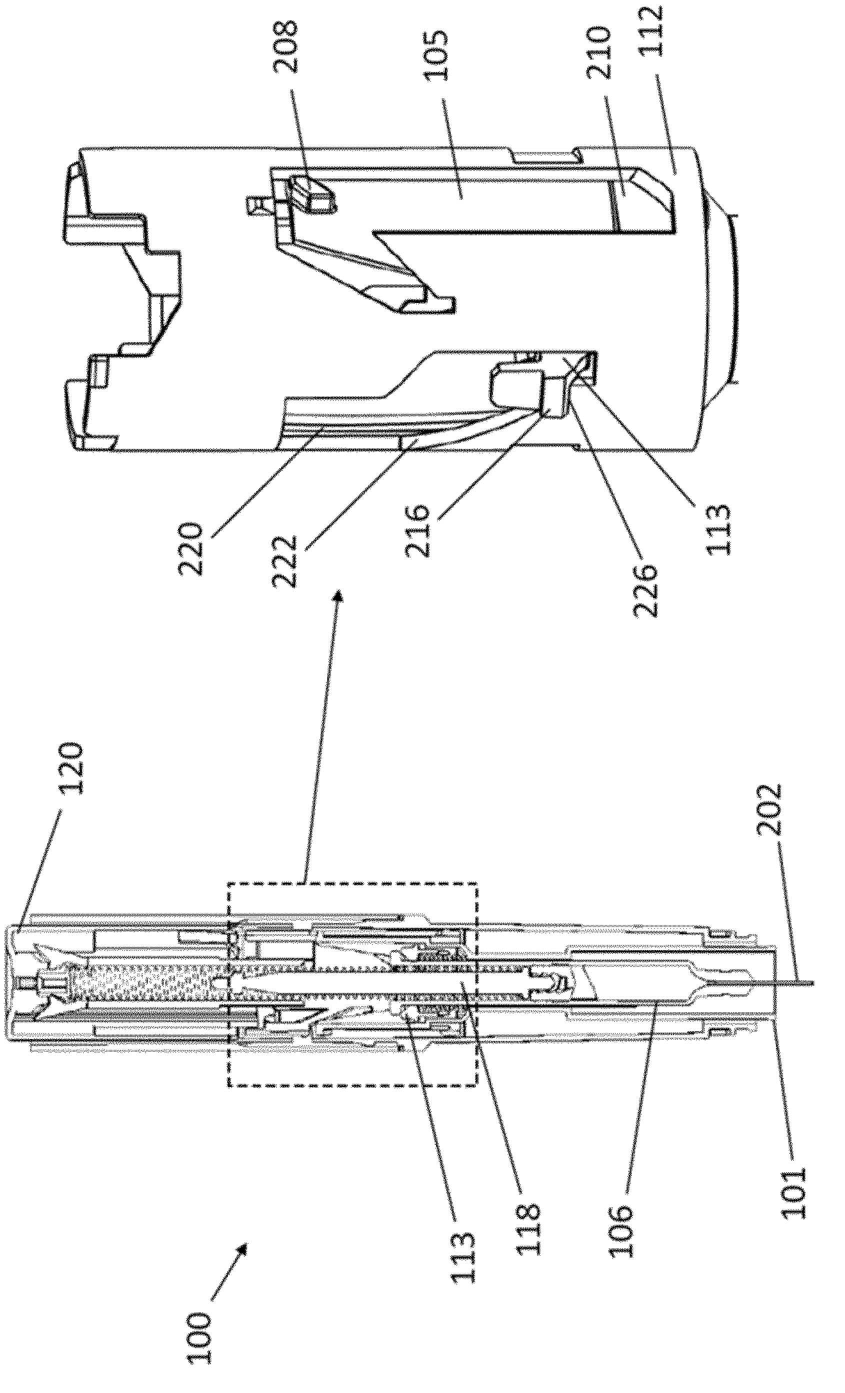
FIG. 5A-5B illustrate an example embodiment of the medicament delivery device in a cross-sectional view of and a detailed perspective view in a state when the injection needle is inserted into the injection site.

Turning now to FIGS. 5A and 5B which illustrate the medicament delivery device when the syringe needle 202 is inserted into the dose delivery site according to an example embodiment. In detail, FIG. 5A is a cross-sectional view of the medicament delivery device 100 and FIG. 5B is a detailed perspective view of the rotator 112, the needle cover 105 and the syringe collar 113 when the syringe needle 202 is inserted into the dose delivery site.

As can be seen in FIG. 5A, after the activation member 120 is actuated as illustrated in FIGS. 4A-4B and described above, the plunger rod 118 travels in the proximal direction within the medicament delivery device 100. When the plunger rod 118 travels in the proximal direction, the plunger rod 118 interacts with the medicament container 106, which medicament container 106 in turn interacts with the syringe collar 113, a proximal end of the plunger rod 118 interacts with the medicament container 106 forcing also the medicament container 106 to be moved in the proximal direction such that the syringe needle 202 protrudes proximally from the proximal end 101 of the medicament delivery device 100. The medicament container 106, which is connected to the syringe collar 113, hereby forces the syringe collar 113 to move in the proximal direction. The needle cover spring 111, i.e. the medicament delivery member spring 110, is here compressed between the syringe collar 113 and the needle cover 105, i.e. the medicament delivery member 104.

As can be seen in FIG. 5B, the syringe collar 113 has been moved in the proximal direction until the radially extending protrusion 216 of the syringe collar 113 arrives and stops at the lower ledge portion 226 of the second axially extending track 220. The axial and proximal motion of the radially extending protrusion 216 thus sets a penetration depth of the syringe needle 202.

When the radially extending protrusion 216 moves in the proximal direction in the second axially extending track 220, the radially extending protrusion 216 engages with the inclined surface portion 222 of the second axially extending track 220, generating a rotation of the rotator 112 in the same rotational direction as the rotation of the rotator 112 generated by the protrusion 208 of the needle cover 105 described above in relation to FIG. 3B. A consequence of the rotation caused by the interaction between the radially extending protrusion 216 and the inclined surface portion 222 of the second axially extending track 220, the needle cover 105 is free to move in the proximal direction when the medicament delivery device 100 is removed from the dose delivery site. Put it differently, the radially extending protrusion 216 of the syringe collar 113 is arranged in abutment with the inclined surface portion 222 of the rotator 112 when the syringe collar 113 follows the inclined surface portion 222, thereby forcing the rotator 112 to be moved in a proximal direction and to rotate around an axially extending geometric center axis 212 of the medicament delivery device 100.

Figure 6:
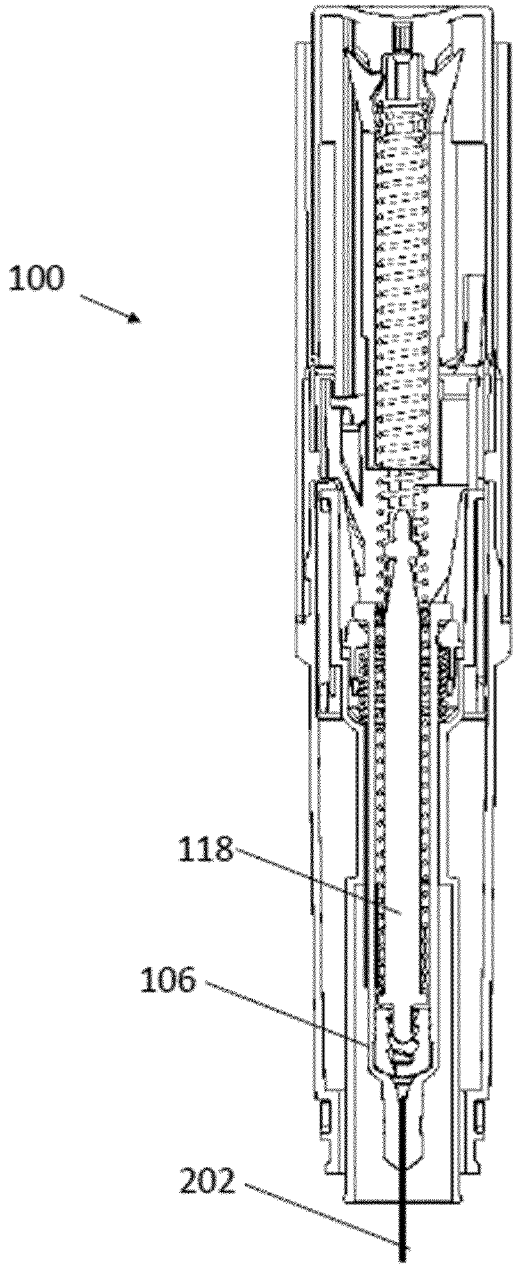
FIG. 6 is a cross-sectional view of the medicament delivery device when injection of medicament to the injection site is finished.

Turning to FIG. 6 which illustrates the final stage of delivering medicament to the dose delivery site. As can be seen in FIG. 6, the plunger rod 118 continues its proximal travel within the medicament container 106 and forces the medicament out through the syringe needle 202. FIG. 6 thus illustrate the stage at which the injection of medicament to the dose delivery site is finished.

Figure 7A:
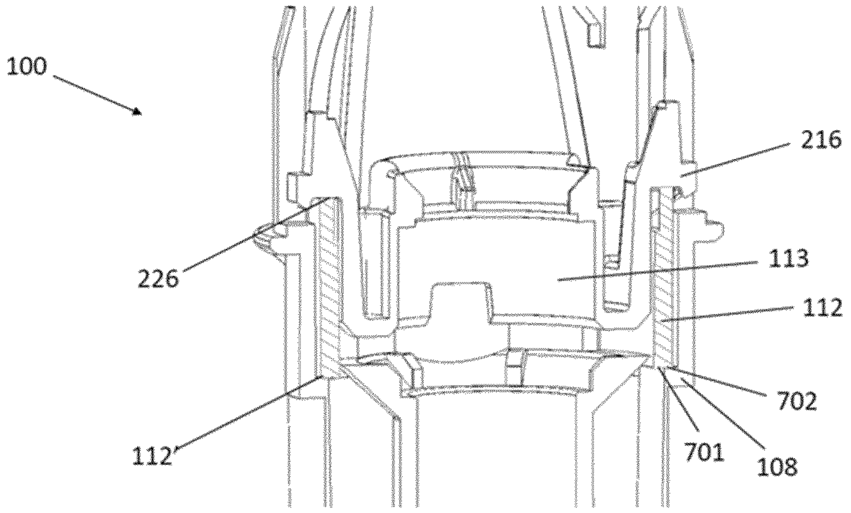
FIG. 7A is a detailed cross-sectional view of the interaction between the syringe collar, the rotator, and the housing when the injection needle is inserted into the injection site according to an example embodiment.
Figure 7B:
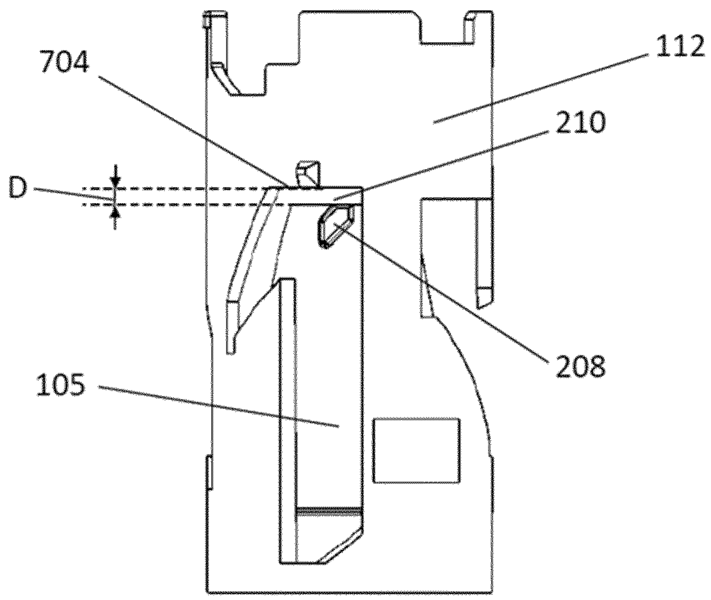
FIG. 7B is a detailed perspective view of the rotator and the medicament delivery member when the injection needle is inserted into the injection site according to an example embodiment.

Reference is now made to FIGS. 7A-7B, of which FIG. 7A is a detailed cross-sectional view of the interaction between the syringe collar 113, the rotator 112, and the first housing portion 108 when the injection needle 202 is inserted into the injection site according to an example embodiment, while FIG. 7B is a detailed perspective view of the rotator 112 and the needle cover 105 when the injection needle is inserted into the injection site according to an example embodiment. Thus, FIGS. 7A-7B correspond to the state which is described above and illustrated in FIGS. 5A-6.

As can be seen in FIG. 7A, the radially extending protrusion 216 of the syringe collar 113 is arranged in abutment with the lower ledge portion 226 of the rotator 112. In turn, the proximal end 112' of the rotator 112 comprises a surface portion 701 arranged in abutment with a distally facing surface portion 702 of the first housing portion 108. Hereby, when the medicament delivery device 100 assumes the protracted state, the force from the syringe collar 113 which is generated by the motion from the plunger rod 118, is absorbed by the first housing portion 108.

With reference to FIG. 7B, the protrusion 208 of the needle cover 105 is arranged at a distance D from a distal end portion 704 of the first axially extending track 210 of the rotator 112. In detail, a distance D is present in the form of an axial gap between the protrusion 208 of the needle cover 105 and the distal end portion 704. Since the needle cover 105 at this stage is in no mechanical contact with the rotator 112, the force generated by the motion of the syringe collar 113 will not be transmitted to the needle cover 105. As such, all of the so called kick back force will be transmitted into the first housing portion 108. Since the first housing portion 108 is connected to the second housing portion 114, the kick back force will be absorbed by the hand of the user holding the medicament delivery device 100 instead of being absorbed by the dose delivery site.

Figure 8:
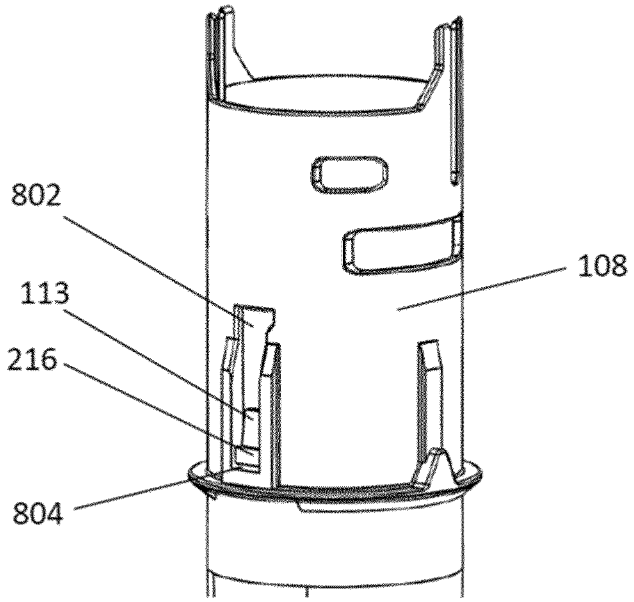
FIG. 8 is a detailed perspective view of the interaction between the syringe collar and the housing when the injection needle is inserted into the injection site according to another example embodiment.

Reference is now finally made to FIG. 8 which is a detailed perspective view of the interaction between the syringe collar and the housing when the injection needle is inserted into the injection site according to another example embodiment.

As can be seen in FIG. 8, the first housing portion 108 comprises an axially extending track 802. The radially extending protrusion 216 of the syringe collar 113 is arranged in the axially extending track 802 and movable within the axially extending track 802 in the axially direction. The axially extending track 802 comprises a proximal end portion 804. This also applies for the embodiment described above in relation to FIGS. 2A-7B. However, in the embodiment depicted in FIG. 8, the radially extending protrusion 216 of the syringe collar 113 is arranged in abutment with the proximal end portion 804 of the axially extending track 802 when the medicament delivery device 100 assumes the protracted state. The movement of the radially extending protrusion 216 of the syringe collar 113 is thus stopped by the proximal end portion 804 of the axially extending track 802, which is different compared to the above described embodiment of FIGS. 2A-7B at which the radially extending protrusion 216 of the syringe collar 113 is arranged in abutment with the lower edge portion 226 of the rotator. The embodiment depicted in FIG. 8 is thus modified in comparison to the embodiment of FIGS. 2A-7B in that the proximal end portion 804 of the FIG. 8 embodiment is positioned closer to the distal end 132 of first housing portion 108 compared to the embodiment of FIGS. 2A-7B. To put it different, the axial distance of the axially extending track 802 is smaller for the FIG. 8 embodiment compared to the corresponding distance for the embodiment depicted in FIGS. 2A-7B. Since the syringe collar 113 is arranged in mechanical contact with the first housing portion, the kick back force will be transmitted into the first housing portion 108, and absorbed by the hand of the user through the first 108 or second 114 housing portions, whichever housing portion the user choose to grip.

The above described FIGS. 2A-4B thus illustrate the medicament delivery device 100 when assuming a retracted state, in which the injection needle 202 is arranged inside the needle cover 105 and prevented from external exposure. Reference is now made to FIGS. 5A-8 which all illustrate the medicament delivery device 100 when assuming a protracted state in which the injection needle 202 protrudes proximally from the proximal end of the needle cover 105.

The inventive concept has mainly been described above with reference to a few examples. However, as is readily appreciated by a person skilled in the art, other embodiments than the ones disclosed above are equally possible within the scope of the inventive concept, as defined by the appended claims.

The invention claimed is:

1. A medicament delivery device configured to expel a medicament from a medicament container comprising an injection needle, the medicament delivery device comprising:

- a housing;
- a medicament delivery member having a tubular body extending along an axis in an axial direction from a proximal end to a distal end, the medicament delivery member comprises an opening configured to receive the medicament container, wherein the medicament delivery member is axially movable within the housing;
- a syringe collar at least partly enclosed by the medicament delivery member, wherein the medicament delivery member and the syringe collar are axially movable within the housing relative to each other; and
- a medicament delivery member spring arranged between, and in contact with, the medicament delivery member and the syringe collar,
- a rotator having a distal end and a proximal end, wherein the rotator is arranged within a portion of the housing,
- wherein the medicament delivery device is configured to assume a retracted state in which the injection needle is arranged inside the medicament delivery member and prevented from external exposure, and a protracted state in which the injection needle is configured to protrude proximally from the proximal end of the medicament delivery member,
- wherein, when the medicament delivery device transitions from the retracted state to the protracted state, the medicament delivery member is arranged stationary relative to the housing and the syringe collar is arranged to move relative to the medicament delivery member in a proximal direction and compress the medicament delivery member spring against the medicament delivery member, and
- wherein the syringe collar is axially locked to a surface portion of the housing when the medicament delivery device assumes the protracted state such that an axial force from the syringe collar, generated during the transition from the retracted state to the protracted state, is absorbed by the surface portion of the housing,
- wherein the proximal end of the rotator comprises a surface portion arranged in abutment with a distally facing surface portion of the housing when the medicament delivery device assumes the protracted state.

2. The medicament delivery device according to claim 1, wherein the medicament delivery member comprises a protrusion at the distal end of the medicament delivery member, the protrusion being arranged in a first axially extending track of the rotator, wherein the protrusion and a distal end portion of the first axially extending track of the rotator are arranged at a distance from each other when the medicament delivery device assumes the protracted state.

3. The medicament delivery device according to claim 2, wherein the syringe collar comprises a radially extending protrusion.

4. The medicament delivery device according to claim 3, wherein the radially extending protrusion of the syringe collar is arranged in abutment with a proximal end portion of an axially extending track of the portion of the housing when the medicament delivery device assumes the protracted state.

5. The medicament delivery device according to claim 4, wherein the radially extending protrusion of the syringe collar is arranged in the axially extending track of the portion of the housing and axially movable along the axially extending track during the transition from the retracted state to the protracted state.

6. The medicament delivery device according to claim 1, wherein the housing comprises a first housing portion and a second housing portion arranged in contact with each other, the first housing portion being arranged to at least partly house the medicament delivery member, and the second housing portion is arranged distally from the first housing portion and configured to be held by a hand of a user.

7. The medicament delivery device according to claim 6, wherein the surface portion of the housing is arranged on the first housing portion.

8. The medicament delivery device according to claim 3, wherein the rotator comprises a second axially extending track, the second axially extending track comprising an inclined surface portion, wherein the radially extending protrusion of the syringe collar is arranged in the second axially extending track and arranged to follow the inclined surface portion when the medicament delivery device transitions from the retracted state to the protracted state.

9. The medicament delivery device according to claim 8, wherein the radially extending protrusion of the syringe collar is arranged in abutment with the inclined surface portion of the rotator when the syringe collar follows the inclined surface portion, thereby forcing the rotator to be moved in a proximal direction and to rotate around an axially extending geometric center axis of the medicament delivery device.

10. The medicament delivery device according to claim 8, wherein the radially extending protrusion of the syringe collar is arranged in abutment with a proximal end portion of the second axially extending track when the medicament delivery device assumes the protracted state.

11. The medicament delivery device according to claim 1, further comprising a plunger rod configured to interact with the syringe collar.

12. The medicament delivery device according to claim 11, further comprising a plunger spring connected to a proximal end portion of the plunger rod, the plunger spring being pre-tensioned when the medicament delivery device assumes the retracted state, and arranged to exert a force on the proximal end portion of the plunger rod to force the plunger rod towards the medicament container during the transition from the retracted state to the protracted state.

13. The medicament delivery device according to claim 1, further comprising an activation mechanism, the medicament delivery device being arranged to transition from the retracted state to the protracted state upon actuation of the activation mechanism.

* * * * *